(12) United States Patent
Haertel et al.

(10) Patent No.: US 11,728,025 B2
(45) Date of Patent: Aug. 15, 2023

(54) AUTOMATIC TRACKING OF PROBABLE CONSUMED FOOD ITEMS (71) Applicant: International Business Machines Corporation, Armonk, NY (US)

(72) Inventors: Stephen Haertel, Ajax (CA); Wing Hon Lee, Richmond Hill (CA); Lior Aronovich, Thornhill (CA)

(73) Assignee: International Business Machines Corporation, Armonk, NY (US)

( * ) Notice: Subject to any disclaimer, the term of this patent is extended or adjusted under 35 U.S.C. 154(b) by 6 days.

(21) Appl. No.: 17/542,382

(22) Filed: Dec. 4, 2021

(65) Prior Publication Data
US 2023/0178213 A1 Jun. 8, 2023

(51) Int. Cl.
G09B 19/00 (2006.01)
G16H 20/60 (2018.01)
A61B 5/00 (2006.01)

(52) U.S. Cl.
CPC ......... G16H 20/60 (2018.01); G09B 19/0092 (2013.01); A61B 5/4866 (2013.01)

(58) Field of Classification Search
CPC .................. G09B 19/0092; G16H 20/60
See application file for complete search history.

(56) References Cited

U.S. PATENT DOCUMENTS

| 6,652,455 | B1 | 11/2003 | Kocher | |
| 11,049,603 | B1* | 6/2021 | Neumann | G16H 50/20 |
| 2007/0059672 | A1 | 3/2007 | Shaw | |
| 2010/0003647 | A1* | 1/2010 | Brown | G09B 19/0092 434/127 |
| 2014/0046677 | A1* | 2/2014 | Bar-Or | G16H 20/30 705/2 |
| 2015/0036138 | A1 | 2/2015 | Watson | |
| 2015/0379238 | A1 | 12/2015 | Connor | |
| 2016/0350514 | A1 | 12/2016 | Rajendran | |

(Continued)

OTHER PUBLICATIONS

"Food Ingredients Scanner, MaxSoft Designed for iPhone", Food Ingredients Scanner on the App Store, 12 pps, Copyright © 2021 Apple Inc. All rights reserved, <https://apps.apple.com/us/app/food-ingredients-scanner/id1459475479>.

(Continued)

*Primary Examiner* — Peter R Egloff
(74) *Attorney, Agent, or Firm* — Aaron Pontikos (57) ABSTRACT

The method provides for detecting information associated with consumed food. Data associated with detection events of food for possible consumption by a user is received from a plurality of sources. The data of detected food is parsed using a first criteria and parsing of event metadata is done using a second criteria and the data received from the detection event. Aggregate data is created for the food items by combining the detected food item data and the respective metadata of the detection event. An ordered list of food items from the aggregate data is generated and arranged according to a determined user consumption probability for the ordered list food items. The aggregate data of respective food items of the ordered list includes nutritional information of macronutrients and calories, accessed from a database, and the list of food items potentially consumed by the user are formatted into a predetermined form.

20 Claims, 3 Drawing Sheets

(56) References Cited

U.S. PATENT DOCUMENTS

2016/0379520 A1* 12/2016 Borel ................. G09B 19/0092
434/127
2018/0082040 A1* 3/2018 Teoh ...................... G16H 40/67
2019/0295440 A1 9/2019 Hadad
2019/0333634 A1 10/2019 Vleugels
2022/0115114 A1* 4/2022 Johnston ............ G06Q 30/0633

OTHER PUBLICATIONS

Jacobsen, "Food Scanners—Will They Change Your Diet?", Futures Platform, Jan. 23, 2018, 4 pps., <https://www.futuresplatform.com/blog/food-scanners-will-they-change-your-diet-calorie-molecular>.
Wiegand, et al., "Knowledge Acquisition with Natural Language Processing in the Food Domain: Potential and Challenges", Published 2012, 6 pps., <https://www.semanticscholar.org/paper/Knowledge-Acquisition-with-Natural-Language-in-the-Wiegand-Roth/dea00c00a252b33b9e4970a006ee137545975bb3?p2df>.

* cited by examiner

AUTOMATIC TRACKING OF PROBABLE CONSUMED FOOD ITEMS

FIELD OF THE INVENTION

The present invention relates generally to the field of information tracking, and more particularly to automatic detection of probable food consumption.

BACKGROUND OF THE INVENTION

Nutritional information and guidance are more abundant, and users are more cognizant of how proper nutrition plays a significant role in personal health and longevity. Nutritional applications for smart devices are prevalent and can provide user feedback based on manual entry of meals, snacks, and drinks consumed. Nutritional applications can determine and track calories of consumed food items as well as nutrients contained in the ingested foods. The applications can indicate whether the consumption of certain nutrients should be encouraged or avoided, and persistent use of nutritional apps and adherence to the guidance of nutritional apps have shown a strong, positive impact on a user's health.

SUMMARY

Embodiments of the present invention disclose a method, computer program product, and system for detecting information associated with consumed food. The method provides for one or more processors to receive data associated with detection of food events for possible consumption by a user from a plurality of sources including audio, image, text, and sensor data. In response to receiving metadata corresponding to the detected food events, one or more processors parse the data of the detected food events o using a predetermined first set of criteria and parsing the metadata received using a predetermined second set of criteria and the data received from the detected event. The one or more processors create aggregate data for a food item of a respective detected event by combining the data of the food item of the respective detected event with the corresponding metadata of the respective detected event. The one or more processors generate an ordered list of food items from the aggregate data arranged by a probability the user has consumed the food items of the ordered list, and wherein the aggregate data of respective food items of the ordered list includes nutritional information of macronutrients and calories, accessed from a database, associated with respective food items, and the one or more processors format the list of food items potentially consumed by the user into a predetermined form.

DETAILED DESCRIPTION

Embodiments of the present invention recognize that establishing and maintaining healthy routines by use of information and following guidance can provide a user improved health. Embodiments recognize that nutritional applications, which collect and track consumed food items and provide the user the nutritional information associated with consumed foods, require significant input on the user's part and diligence in performing manual entry in order to reap the benefits offered by the nutritional application. Embodiments also recognize that the tedious and repetitious manual entry of consumed food items by a user can eventually result in the user abandoning the entry and forfeiting the benefits offered by a nutrition-based personal application. Embodiments recognize a need for automatically detecting and tracking food items with a high probability of consumption by the user. The automatic detection and tracking reduce the amount of manual entry by identifying and preparing food item data that can be output to a nutritional application. Embodiments further realize that by reducing the amount of manual entry required, the likelihood of a user maintaining a routine of tracking consumed foods improves, and the health benefits for the user are realized.

Embodiments of the present invention minimize the manual steps involved in tracking by providing a computer-implemented process, computer program product, and computer system for detecting food items for consumption by a user. In some embodiments, a plurality of detection sources provides input data, including audio, text, image, API, and physical sensor input sources. Recognition of a food detection event provides input data and includes data indicating or identifying a food item that has a probability associated with the food item being consumed by the user. A food detection event includes the capture of data associated with a food item by a detection source and includes data used to identify the food item as well as metadata associated with the food detection event. The metadata is received and includes, but is not limited to, information regarding the time of the food detection event, the location of the food detection event, purposeful sharing of API metadata from other applications, and additional applications operating on the user's device.

In some embodiments, parsing operations performed on the received food item detection data and metadata enable identification of food items or triggering items included in the data received from the food detection event. Additionally, parsing of the received metadata enables the separation of information elements such as, but not limited to, the time, location, and information from other applications for alignment with food identification from the detected food event. In some embodiments, a food detection program (herein, food detection program 200 discussed below) aggregates the identified food item and corresponding metadata into a set of information and data for the respective food detection events.

The food detection program 200 analyzes the set of information and data and calculates and assigns weights to produce a score for each type of metadata and an overall score. In some embodiments, a comparison of metadata of prior instances of food detection events and current metadata of current food detection events determines whether similarity exists and the appropriateness of applying additional weights to the determination of scores.

Having determined the individual metadata components scores, food detection program 200 determines a final score for respective food items. The scores represent a probability that the food item was consumed by the user. The food items are sorted by respective scores exceeding a pre-determined threshold indicating a probability that respective food items were consumed by the user and may be presented in a highest to lowest order, for example. The automatic determination of the probability of consumption of a food item reduces the persistent requirement of a user to manually enter consumed food data for a nutritional-based application. In some embodiments, including initial instances of food detection events without larger quantities of historic food detection events, a verification step presents the sorted list of food items exceeding a predetermined threshold score for user confirmation. In other embodiments in which significant history of food detection events exists, an optional verification step may not be elected by the user. In some embodiments, an optional combination of the sorted list of consumed food items with corresponding nutritional information for the respective food items can be selected, in which available online nutrient databases provide the nutritional information. The optionally combined list and nutritional information are further formatted as output to a nutritional app.

Figure 1:
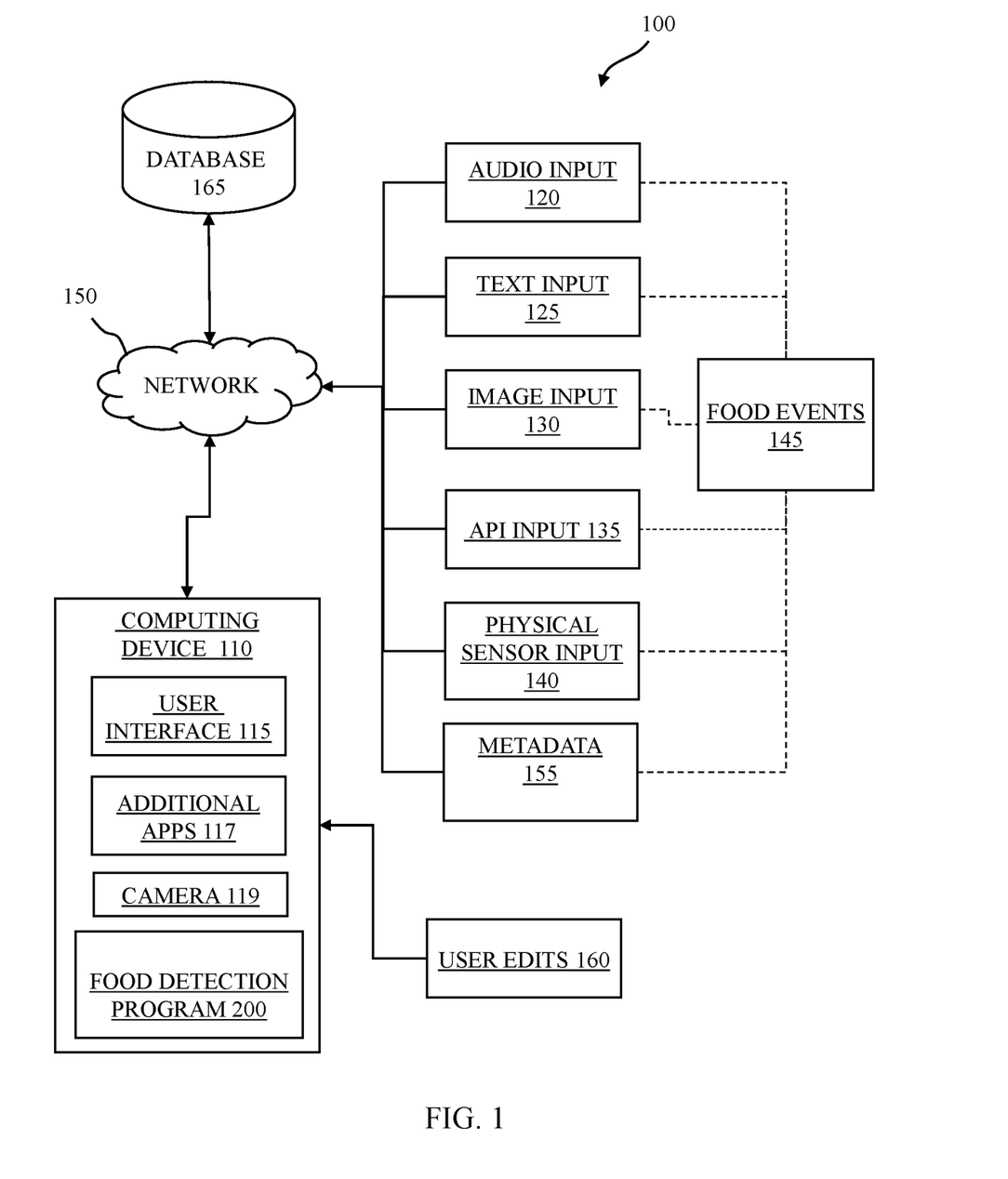
FIG. 1 is a functional block diagram illustrating a distributed data processing environment, in accordance with an embodiment of the present invention.

The present invention will now be described in detail with reference to the Figures. FIG. 1 is a functional block diagram illustrating a distributed computer processing environment, generally designated 100, in accordance with an embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed computer processing environment 100 includes computing device 110, sources of audio input 120, text input 125, image input 130, API input 135, physical sensor input 140, metadata 155, and database 165, all interconnected via network 150. Distributed computer processing environment 100 also includes user edits 160 and food events 145. Network 150 can be, for example, a local area network (LAN), a wide area network (WAN), such as the Internet, a virtual local area network (VLAN), or any combination that can include wired, wireless, or optical connections. In general, network 150 can be any combination of connections and protocols that will support communication and data transmission.

Computing device 110 includes user interface 115, additional apps 117, camera 119, and food detection program 200. In some embodiments, computing device 110 can be a blade server, a web server, a laptop computer, a desktop computer, a standalone mobile computing device, a smartphone, a tablet computer, or another electronic device or computing system capable of receiving, sending, and processing data. In other embodiments, computing device 110 may be a wearable item or be included in a wearable item of a user, such as augmented reality (AR) glasses. In still other embodiments, computing device 110 may be a computing device interacting with applications and services hosted and operating in a cloud computing environment. In another embodiment, the computing device 110 can be a netbook computer, a personal digital assistant (PDA), or other programmable electronic devices capable of receiving data from and communicating with other devices (shown and not shown) in distributed computer processing environment 100, via network 150, as well as performing operations of food detection program 200. Alternatively, in some embodiments, computing device 110 may be communicatively connected to food detection program 200, operating remotely. Computing device 110 may include internal and external hardware components, depicted in more detail in FIG. 3.

User interface 115 provides an interface to access the features and functions of computing device 110. In some embodiments of the present invention, user interface 115 provides access to operate and select options for food detection program 200 and may also support initiation and interaction with additional apps 117 installed on computing device 110, as well as access features and functions of computing device 110 (not shown). In some embodiments, user interface 115 provides display output and input functions for computing device 110. In other embodiments, user interface 115 provides a display of output by food detection program 200 for optional verification by the user of computing device 110.

User interface 115 supports access to alerts, notifications, and provides access to forms of communications. In one embodiment, user interface 115 may be a graphical user interface (GUI) or web user interface (WUI) and can receive user input and display text, documents, web browser windows, user options, application interfaces, and instructions for operation, and include the information (such as graphic, text, and sound) that a program presents to a user and the control sequences the user employs to control the program. In another embodiment, user interface 115 may also include mobile application software that provides respective interfaces to features and functions of computing device 110. User interface 115 enables respective users of computing device 110 to receive, view, hear, and respond to input, access applications, display content of online conversational exchanges, and perform available functions.

Additional apps 117 operate from computing device 110 and provide the user of computing device 110 additional features and functions. Additional apps 117 represents one or more added applications to computing device 110 and, in some embodiments, include apps for ordering food items and/or searching for food items on a menu associated with a restaurant or, generically, a food eatery. Additional apps 117 may include data within the application and/or display memory that includes images, text, or audio of food items, which may be detected by one or more input sensor sources that listen to or monitor inputs and activity of additional apps 117.

Camera 119 provides an image capturing component of computing device 110. In some embodiments, camera 119 is configured to provide video image monitoring and can capture images of objects and areas that may include food items or text identifying or describing food items. In some embodiments, camera 119 can be a set of imaging sensors located on a user (e.g., included in a wearable item, attached to the user as jewelry or accessory, or included in smart glasses), or around a user (e.g., set of mini drones capturing images of the user's surrounding and user's activity). Camera 119 transmits captured images to food detection program 200 for analysis to determine trigger images or objects indicating a trigger of a food item.

Food detection program 200 produces an ordered listing of food items and information, based on a probability threshold that the user of computing device 110 consumes the detected food item. Food item scores are calculated, based on metadata corresponding to the food item detected from a food detection event, as well as the similarity data of food items from prior food detection events maintained in a history database. Scores exceeding a pre-determined threshold are included in the ordered list and formatted as output, compatible as input to a nutritional application, which reduces the amount of manual entry by a user of the nutritional application.

Food detection program 200 offers a user an opt-in selection granting permission to receive and use the data gathered from multiple input sources for determining food detection events and food items. Food detection program 200 confirms the opt-in selection and receives data of a food detection event from multiple sources including audio input 120, text input 125, image input 130, API input 135, and physical sensor input 140. Additionally, food detection program 200 receives metadata corresponding to an event of food events 145. Non-limiting examples of the metadata includes the time associated with the food detection event, the location and proximity distances associated with the food detection event, and information of additional apps associated with the food detection event. Food detection program 200 parses the received data according to a predetermined first set of criteria and parses the metadata according to pre-determined second set of criteria. The first set of criteria includes comparing detection data to a corpus of food item and food-related terms, phrases, images, and objects assembled into a local or accessible external database, such as database 165. Food detection program 200 identifies a food item of a food detection event by locating a parsed term, phrase, image, or object within the pre-determined first criteria corpus of terms and phrases. The second set of criteria includes, but is not limited to, recorded time data corresponding to the food detection event, location and proximity at the time of the food detection event, and application input from parallel operating apps on the user's device. Food detection program 200 identifies the food item(s) and metadata associated with the food detection event, and determines quantities of the food item, if available, as well as detecting other users present at the time of the food detection event.

Food detection program 200 aggregates the parsed data combining a respective identified food item with the corresponding metadata elements of the food detection event. The aggregation pairs the identified food item with the time, location of the food detection event, and may include the presence of other users as well as information indicating a quantity of the food item(s). Food detection program 200 calculates a score for the metadata components and determines an overall final score that correlates to a probability that the food item was consumed by the user. Food detection program 200 determines the final score and the corresponding probability of user consumption of the food item exceeds a pre-determined threshold and includes the food item in a listing of probable consumed items, ordered by the probability level of consumption.

In some embodiments, food detection program 200 optionally accesses the nutritional information associated with the food items from available online data sources and includes the information with the food items. In some embodiments, food detection program 200 offers a validation step for the user, presenting the ordered listing of probable consumed food items and enabling the user to confirm or reject respective food items as consumed. In some embodiments, food detection program 200 prepares the ordered list of probable (or confirmed) food items as output, which includes formatting as acceptable input received by a nutritional application.

Audio input 120 includes one or more sensors listening to audio sources and extracts spoken content detected. Audio input 120 transmits the detected content to food detection program 200 for parsing of the audio input to identify food entities mentioned in the extracted spoken language of the user. In some embodiments, audio input 120 includes trained voice recognition of the owning user of audio input 120 sensors and distinguishes voices of other users. In some embodiments, audio input 120 includes detection of chewing sounds that indicate a high probability of consumption of food items detected in the same time proximity of the chewing sounds. In some embodiments, the user of computing device 110 improves the effectiveness of food detection program 200 and audio input 120 by vocally reciting food items consumed.

In some embodiments, audio input 120 buffers a small amount of extracted spoken language in the event that food detection program 200 detects a food item, so that the audio preceding the detected food item can be analyzed to determine quantities of the food item. Subsequent to detection of a food item by the recognition of a trigger word by food detection program 200, audio input 120 records audio for a configurable short period of time, such as for 4-8 seconds, for example. Recording continues if additional trigger words are detected by food detection program 200, up to a pre-defined maximum time. Food detection program 200 identifies trigger words by accessing a database that associates words and phrases with food items, food symbols and images, and food eateries, and compares detected input to the trigger data of the database. Detection of food items and/or eateries triggers recognition of a food detection event by food detection program 200.

Text input 125 monitors the text content of user interface 115 of computing device 110 as well as the memory cache of text content received and available but not currently displayed (i.e., content requiring scrolling on a user's device display). Text input 125 transmits monitored text content to food detection program 200 operating on computing device 110 for parsing of the transmitted content, extraction, and detection of food items, food establishment (generic or named), and quantities of food items. Detected food items and quantities as well as food establishment detection triggers a food detection event.

Image input 130 monitors the immediate environment through camera 119 or other imaging sensors (not shown) for images and written text of food items and/or food eateries appearing in captured images. Camera 119 may be included as a component of computing device 110 as depicted in FIG. 1 or may be remote and include wearable imaging sensors or image capturing drones communicatively connected to food detection program 200 via computing device 110. Food detection program 200 receives the monitored data transmitted from image input 130 and parses the monitored data to detect and extract food items, quantities of food items, as well as food establishment names. The detection is accomplished by object recognition techniques involving machine learning, applied to the transmitted image data by food detection program 200. Image input 130, parsed by food detection program 200 includes the detected food item and possible detection of food establishments and quantities but does not include the image itself. Detected food items and/or food establishments trigger a food detection event with food detection program 200.

API input 135 provides an input path of data from other sources such as additional apps 117 resident on computing device 110. API input 135 receives food item, quantity data, and metadata in a known format presented to the public, such as from a similar or competing application connecting with API input 135 and providing a source of consumed food items that can be assumed to exceed the pre-determined probability threshold.

Physical sensor input 140 provides a source of data that detects physical aspects of food consumption, such as sensors that monitor changes to chemicals in the bloodstream, detection of gastric activity, detection of chewing followed by swallowing, etc. Physical sensor input 140 may include nano-sized devices within a user that can provide monitoring data. Data monitored by physical sensor input 140 is received by food detection program 200 for parsing and identification of food items and/or quantities. In some embodiments, an external device that identifies a food item by odor/scent detection (i.e., sniffer) may be communicatively connected to food detection program 200 and transmit data from the external physical device. Detection of food items via physical sensor input 140 triggers a food detection event with food detection program 200.

Food events 145 represents a plurality of activity and situations in which a user of computing device 110 performs an activity that includes detection of a food item and/or a food establishment by an input source transmitting the input to food detection program 200 for parsing and food item detection. Food events 145 can include but are not limited to, image and audio input of preparing a meal at a user's home, ordering food on a phone call or in a food establishment, texting an order of food from a smart device, ordering food from an app, scanning of a menu, commenting on the taste or quality of a named food item, recognition of a sign of a food establishment (and entering the establishment), and other monitored activities.

Metadata 155 includes data associated with a detection of a food time triggering a food detection event. Metadata 155 includes data associated with the time of the food item detection, the location and proximity of the food item detection, and may include determining the quantity of the food item detected. In some embodiments, data from other applications running on a user's smart device, such as computing device 110, provides metadata associated with the provided data input of food detection, such as the establishment associated with an ordering application and the history of the user placing orders via the application. Embodiments of the present invention use metadata 155 to calculate a score associated with respective food detection events in which the score of the food item of the food detection event corresponds to a probability that the food item was consumed by the user.

In some embodiments, user edits 160 is available as an option to verify the consumption of the detected food items. In some embodiments, food detection program 200 generates an ordered list of food items detected and determined to have a score exceeding a pre-determined threshold, which indicates a higher probability that the respective food items were consumed by the user. In some embodiments, a user accesses user edits 160 and confirms or rejects the listed food items as consumed. In other embodiments, in which the user has an extensive history using food detection program 200 and food detection program 200 has improved accuracy and effectiveness in determining consumed food items, user edits 160 may prove unnecessary.

Database 165 includes a corpus of food terms and phrases as well as storing food detection events and associated food item/establishment input data, metadata, and confirmation of consumption if provided. Food detection program 200 accesses database 165 to determine if parsed terms and phrases are associated with a food item or a type of food establishment. In some embodiments, historic records of food detection events are accessed by food detection program 200 to determine similarity with a current food detection event, which may be based on timing, location, type of food item, or combinations of food item and metadata, food detection program 200 assigns additional weight to the score and final score of the food detection event indicating a higher probability of consumption of the food item.

Triggering of a food detection event results from food detection program 200 identifying a food item and/or food establishment from the received input. A food detection event collects additional input as metadata associated with the input of the food detection event. The metadata includes capturing the time of the food detection event, which may include time-of-day, day-of-the-week, and may include seasonal information. The time metadata is captured by a device that includes an internal time tracking function, such as a smartphone, tablet, smartwatch, and computing device 110. The metadata associated with the detected food detection event also includes location information.

In some embodiments, the location may be from a global positioning system (GPS) operating on a computing or smart device, such as computing device 110. The GPS data may be in the format of GPS coordinates, and/or may be provided to an online mapping application that determines the businesses and features associated with the coordinates, such as a restaurant, a user's home, or a shopping mall (that includes a food court). In some embodiments, metadata collected in association with a food detection event also includes purposeful sharing of application programming interfaces (APIs) in food detection program 200 to receive food items and source information from other applications.

Figure 2:
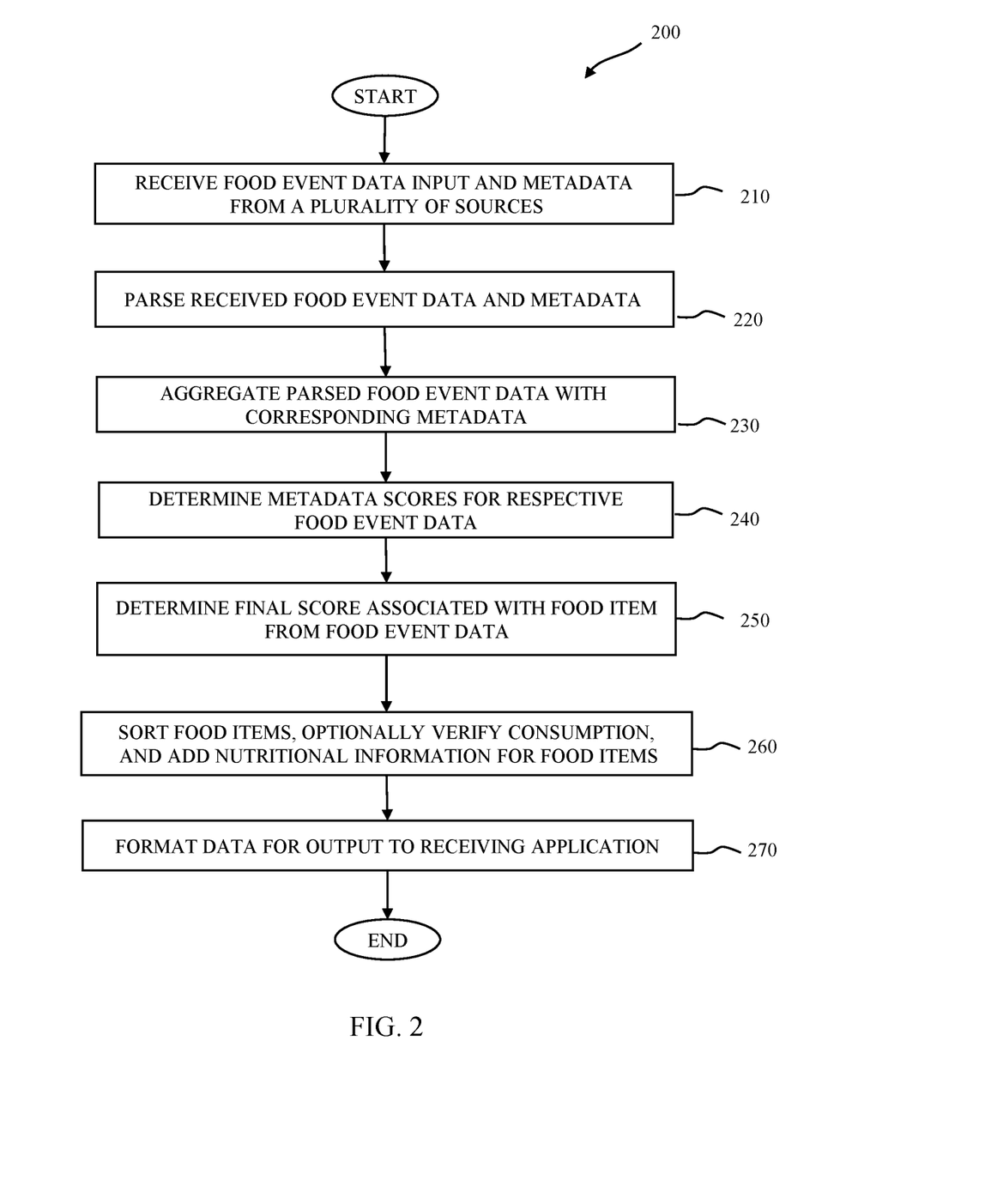
FIG. 2 depicts a flowchart of the operational steps of a food detection program, in accordance with an embodiment of the present invention.

FIG. 2 depicts a flowchart depicting the operational steps of food consumption program 200 operating in distributed computer processing environment 100 of FIG. 1, in accordance with embodiments of the present invention.

Food detection program 200 receives food event data input and metadata from a plurality of sources (step 210). Food detection program 200 receives input data from sources monitoring audio of a user's immediate surroundings, images of the user's immediate surroundings, text on the display and memory of a smart device of the user, input from external applications via APIs of food detection program 200, and physical sensors that monitor the user's condition and actions. Food detection program 200 analyzes the input to determine a food detection event. The received input also includes metadata associated with the monitored input, such as the time associated with the monitored input, the location of the monitored input, and recognition of other users in the vicinity of the monitored input. In some embodiments, the metadata includes additional metadata from other apps running on the user's device and can include metadata received from detection of food items by other applications external to the user's device. The other application input will be recorded along with a food item detection to add weight to food items that may be detected, for example, as a result of ordering food from an app on a smartphone. A food item entry detected in the text on a screen when a food ordering application is running will be given more weight regarding the probability of consumption than when a normal internet browser is running by itself, for example. A database of applications coupled with their relevancy will be stored on the user device, such as computing device 110, or accessed by remote connection via network 150, such as database 165, and the application and relevancy data will be able to be updated over time.

For example, food detection program 200, operating on computing device 110, received external input data from audio input 120, text input 125, image input 130, API input 135, and physical sensor input 140. Additionally, food detection program 200 receives metadata 155 associated with the monitoring for a real-time food detection event, such as food events 145, and input from an app of additional apps 117 including a food item ordered using the app.

Food detection program 200 parses the received food event data and metadata (step 220). Food detection program 200 performs parsing operations on the received external input data and metadata. Food detection program 200 compares the terms and phrases determined from the parsing and interpretation operations to a corpus of food items and food establishment terms in an accessible database. In some embodiments, the audio input is converted via natural language processing (NLP) techniques to digitized terms and phrases suitable for search and comparison with database terms and phrases. Similarly, food detection program 200 processes the image input data for recognition of text and/or objects within the image and compares the input to object and text data of the corpus included in the database. Food detection program 200 performs similar comparisons with input data received from APIs and physical sensors and identifies a food detection event based on identifying food item terms or phrases and/or food establishments.

Food detection program 200 parses the received data according to a predetermined first set of criteria and parses the metadata according to a predetermined second set of criteria. The first set of criteria includes a corpus of food items and food-related terms and phrases, assembled into a local or accessible external database, such as database 165. Food detection program 200 identifies a food item of a food detection event by locating a parsed term or phrase within the pre-determined first criteria corpus of terms and phrases. The second set of criteria as a non-limiting example, includes recorded time data corresponding to the food detection event, location and proximity at the time of the food detection event, and application input from parallel operating apps on the user's device.

For example, food detection program 200 parses the external input data from audio input 120, text input 125, image input 130, API input 135, and physical sensor input 140, as well as metadata 155. Food detection program 200 identifies food items and/or food establishments indicating a food detection event, and parses the metadata received, including time of the food detection event, location and proximity of the food detection event, and input from concurrently running applications on computing device 110.

Food detection program 200 aggregates parsed food item data with corresponding metadata (step 230). Food detection program 200 combines the identified food item and the corresponding metadata of the food detection event into an aggregate set of data. A local database, or external database accessible via network 150 to food detection program 200, stores the combined set of data. Food detection program 200 combines each identified food item detected with the corresponding metadata associated with the food item. The food item and metadata are aggregated as a set of data associated with a food detection event. Metadata includes time, (i.e., time of day, week, month, season), and location/proximity of the food detection event. In some embodiments, metadata includes input indicating quantities of the food item and detection of additional users, which may indicate a greater likelihood of food item consumption if users are known to be present during historic food detection events with confirmed consumption of food items.

The metadata will enable weighting associated with a food detection event indicating a higher likelihood that the detected food item is consumed. Food detection program 200 accesses past entries of food detection events, including manual edits to past final output data by the user, to determine the likeliness of future events. In addition, relatively recent past food detection input events that have not yet been fully processed will also be taken into account to boost the confidence of others. If a food and a quantity of food have been detected to have been eaten in the past, then a greater likelihood exists for the food item to be eaten in the future.

Food detection program 200 determines metadata scores for respective food detection event data (step 240). Food detection program 200 performs analysis on the metadata of the food detection event. An unspecified quantity of the food item results in a default value for the quantity estimated from database entries of the same or similar food item, and subsequently from historic food detection event aggregate data. The metadata scores contribute to determining the probability of consumption of the food item by the user. The calculation of the time metadata contribution to the score compares the actual time of the food detection event to known times the user typically eats, with greater weight given to food detection event times closer to the user's known eating times, and lesser weight given to times removed from the user's known eating times. An example expression is: Time score $(S_T)$=function $(Time_{current}, w)$.

Food detection program 200 determines the location metadata contribution to the score for the food item associated with the food detection event (referred to also as "a/the event") by determining the proximity of the event to known eating establishments or previous places the user has eaten in the past (determined from location history of the user's device and/or previous food detection event data saved to a local database). The score contributed by the location metadata can be expressed as: Location score $(S_L)$=function $(d_1, d_2, \ldots d_N)$.

The score contributed by the detection of a food item of the event by other applications running on the device can be calculated from a pre-existing table of application types. The metadata of a food detection event detected by simply browsing the internet would not contribute a score as high as that of a known food-ordering application. The parallel running application metadata determines the contributing score as a function of the application type scores from a local or remote database, which can be revised over time. The application type metadata score can be expressed as Application score $(S_A)$=function $(S_1, S_2, \ldots S_N)$, where $S_1$, $S_2, \ldots S_N$ have assigned values based on the type of application. For example, a food ordering application has a higher score value than a web browser application.

The score contributed by past data will be calculated as a function of the similarity to the newly detected event. This past data will come from a local or remote database of past entries. Examples of past input data being compared include the input of food detection events that have already been finalized and completed, as well as food detection events that have been detected in relatively quick succession such as an event input triggered by a physical sensor in the order of seconds after an audio input trigger.

Calculation of a past entry of a food detection event similarity score includes a value indicating whether the past entry was completed $(C_1)$ and includes determining similarity as a function of the food type and associated metadata. For example, Similarity $(S_1)$=function (Food, $M_1, M_2, M_3$), where $M_1$=function $(Time_{current}, Time_{previous})$; $M_2$=function $(Location_{current}, Location_{previous})$; and $M_3$=function $(App_{current}, App_{previous})$. The past input score can then be expressed as a function of the determined similarity scores: Past Input Score $(S_P)$=function $(S_1, S_2, \ldots S_N)$. The score contributed by all past input data $(S_P)$ is a function of the scores from individual past input data ($S_N$). The score of an individual past input data event is a function of the similarity between it and the current data input event being compared ($Sim_N$) along with whether or not the events have been completed ($C_N$).

Food detection program 200 determines a final score associated with the food item of the food detection event data (step 250). Having calculated the scores for metadata components for the food detection event, food detection program 200 determines a final score associated with the food item and indicates the probability the food item is consumed by the user. A function of the metadata determines the final score of the food item(s) and includes at least a time score, a location score, an application score, and a past input score expressed as Final Score=function ($S_T$, $S_L$, $S_A$, $S_P$). Food detection program 200 aligns the scoring schema to the probability of the user consuming the food item associated with the food detection event, such that a higher final score is consistent with a higher probability of consumption.

For example, metadata score calculations associated with a food detection event may include a time attribute of 12:15 p.m., a location attribute that corresponds to one of the user's frequented restaurants, the application attribute may not have been used and is void of data, and the past history attribute recognizes a match with an audio input of a meal name, such as "the downtown club sandwich." The metadata scores may be setup as ranging from 0 to 1, with 1 indicating certainty of the user consuming detected food items, and 0 indicating certainty the user did not consume the detected food items.

Food detection program 200 determines a final score based on the time attribute aligning with a time of day the user typically eats, with a $S_T$ score of 0.85, a location attribute aligned with a frequented restaurant giving a $S_L$ score of 0.80; an application attribute score ($S_A$) of 0.00 since no input was received by an API from another application, and because the ordered meal detected from audio input data matched a meal name the user has ordered previously (more previous instances=higher $S_P$ score) the $S_P$ metadata score is 0.75. Food detection program 200 applies a function to $S_T$, $S_L$, $S_A$, $S_P$ which, in the example may be an average score of the contributing metadata scores for the food detection event (0.85+0.80+0.75)/3=0.80. The final score may directly correspond to a probability of consumption of the food item by the user, in this example, 80%. Food detection program 200 compares the final score for the food item of the food detection event to a configurable threshold value, such as 65% and determines the food item as having been consumed by the user. In some embodiments, the configurable threshold value is set at a percentage value above 50% and is adjusted over time based on accuracy levels of determining food consumption, with the threshold increasing as accuracy improves.

Food detection program 200 sorts food items, optionally verifies consumption of food items, and adds nutritional information of the food items (step 260). Having determined the final score associated with each food item of respective food detection events, food detection program 200 organizes the aggregate data associated with respective food items ordering the items based on the final scores corresponding to the probability of consumption by the user. For example, food detection program 200 orders the aggregate data from highest probability to lowest probability of consumption. In some embodiments, food detection program 200 compares the food item probabilities (or final scores in a parallel approach) to a pre-determined threshold and retains the ordered food item aggregate data exceeding the threshold and deleting or indicating a sub-threshold condition for the remaining food item aggregate data.

In some embodiments of the present invention, food detection program 200 optionally presents the sorted food item aggregate data to the user of computing device 110 to review and verify the food items determined as consumed. The user confirms or rejects the listed food items of the aggregate data and confirms the completion of the verification. In some embodiments, food detection program 200 200 omits the optional user verification, having performed significant numbers of scoring food detection events and having accrued a large number of past food detection events.

Food detection program 200 formats food item identities and data for output to receiving application (step 270). Food detection program 200 performs a formatting operation preparing the food item aggregate data exceeding the threshold for output to an external nutritional application receiving the food item aggregate data in the format prepared by food detection program 200. Having prepared formatted output, food detection program 200 ends. Optionally, in some embodiments, food detection program 200 may access and extract additional nutritional data for the food items in the aggregate data formatted for output to an external application.

Figure 3:
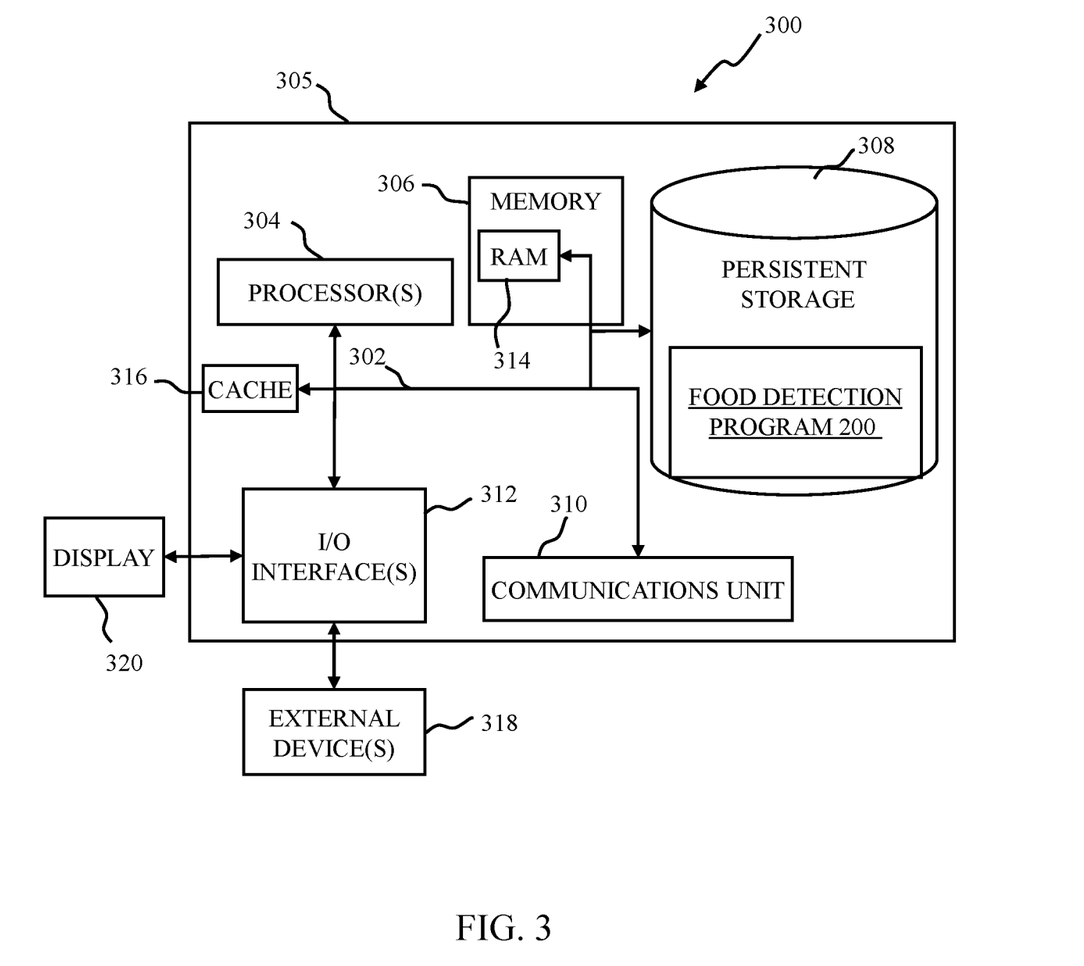
FIG. 3 depicts a block diagram of components of a computing system, including a computing device configured to operationally perform the food detection program of FIG. 3, in accordance with an embodiment of the present invention.

FIG. 3 depicts a block diagram of components of computing system 300, including computing device 305, configured to include or operationally connect to components depicted in FIG. 1, and with the capability to operationally perform program 200 of FIG. 2, in accordance with an embodiment of the present invention.

Computing device 305 includes components and functional capability similar to components of computing device 110 (FIG. 1), in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Computing device 305 includes communications fabric 302, which provides communications between computer processor(s) 304, memory 306, persistent storage 308, communications unit 310, an input/output (I/O) interface(s) 312. Communications fabric 302 can be implemented with any architecture designed for passing data and/or control information between processors (such as microprocessors, communications, and network processors, etc.), system memory, peripheral devices, and any other hardware components within a system. For example, communications fabric 302 can be implemented with one or more buses.

Memory 306, cache memory 316, and persistent storage 308 are computer-readable storage media. In this embodiment, memory 306 includes random access memory (RAM) 314. In general, memory 306 can include any suitable volatile or non-volatile computer-readable storage media.

In one embodiment food detection program 200 is stored in persistent storage 308 for execution by one or more of the respective computer processors 304 via one or more memories of memory 306. In this embodiment, persistent storage 308 includes a magnetic hard disk drive. Alternatively, or in addition to a magnetic hard disk drive, persistent storage 308 can include a solid-state hard drive, a semiconductor storage device, read-only memory (ROM), erasable programmable read-only memory (EPROM), flash memory, or any other computer-readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer-readable storage medium that is also part of persistent storage 308.

Communications unit 310, in these examples, provides for communications with other data processing systems or devices, including resources of distributed data processing environment 100. In these examples, communications unit 310 includes one or more network interface cards. Communications unit 310 may provide communications through the use of either or both physical and wireless communications links. Food detection program 200 may be downloaded to persistent storage 308 through communications unit 310.

I/O interface(s) 312 allows for input and output of data with other devices that may be connected to computing system 300. For example, I/O interface 312 may provide a connection to external devices 318 such as a keyboard, keypad, a touch screen, and/or some other suitable input device. External devices 318 can also include portable computer-readable storage media such as, for example, thumb drives, portable optical or magnetic disks, and memory cards. Software and data used to practice embodiments of the present invention, e.g., food detection program 200 can be stored on such portable computer-readable storage media and can be loaded onto persistent storage 308 via I/O interface(s) 312. I/O interface(s) 312 also connects to a display 320.

Display 320 provides a mechanism to display data to a user and may, for example, be a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer-readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other devices to cause a series of operational steps to be performed on the computer, other programmable apparatus, or the other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for detecting a food item consumed by a user, the computer-implemented method comprising:

receiving, by one or more processors, input data associated with possible food items for consumption by a user from at least one input source, wherein, the at least one input source includes a sensor communicatively connected to the one or more processors;

triggering, by the one or more processors, a food detection event, based on the input data received from the sensor communicatively connected to the one or more processors;

in response to receiving metadata corresponding to the food detection event, parsing, by the one or more processors, the input data of the food detection event using a predetermined first set of criteria, and parsing the metadata received using a predetermined second set of criteria, wherein the received metadata includes a time and a location of the food detection event associated with available shared data from parallel applications and application programming interfaces (APIs) communicatively connected to the one or more processors during the food detection event;

creating, by the one or more processors, aggregate data for a first food item identified from a first food detection event by combining first input data of the first food item with the corresponding metadata of the first food detection event;

calculating, by the one or more processors, a first score associated with a probability the first food item of the first food detection event is consumed by the user; wherein calculation of the first score includes weighting factors determined from the metadata input of time, location, external applications, and past input data of prior confirmed food detection events, wherein calculation of the first score includes the input data received from the sensors and weighting factors determined from the metadata including the available shared data;

generating, by the one or more processors, an ordered list of the food items arranged by scores from the aggregate data of the food detection events, including the first food item from the first food detection event arranged by the first score; and formatting, by the one or more processors, the ordered list of the food items consumed by the user into a predetermined form.

2. The computer-implemented method of claim 1, wherein the predetermined first set of criteria includes a corpus of food terms and phrases that is accessed to identify food items by comparison of the input data to the corpus of food terms and phrases, and the predetermined second set of criteria includes recorded time data corresponding to the food detection event, location and proximity at the time of the food detection event, and application input from parallel operating apps on a user's device.

3. The computer-implemented method of claim 1, wherein the input data from at least one of the plurality of sources include the input data from a group consisting of audio input data, image input data, text input data, and physical sensor input data.

4. The computer-implemented method of claim 1, wherein the first score associated with the probability the first food item is consumed by the user further comprises:

determining, by the one or more processors, a time score for a time element of the metadata based on a comparison of the time associated with the first food detection event and known times the user typically eats;

determining, by the one or more processors, a location score for a location element of the metadata based on a proximity of the location of the first food detection event to a location of known food establishments;

determining, by the one or more processors, an app score for other applications of the metadata based on a type of the other applications; and determining, by the one or more processors, a past data score for past data of the confirmed prior food detection events, based on completion status and similarity of event metadata compared to the metadata associated with the first food detection event.

5. The computer-implemented method of claim 1, further comprising:

defining, by the one or more processors, a pre-determined threshold score associated with the probability that the user consumed the first food item;

determining, by the one or more processors, whether a final score associated with the first food item of the first food detection event exceeds the pre-determined threshold score associated with the probability that the user consumed the first food item; and in response to determining the final score associated with the first food item of the first food detection event exceeds the pre-determined threshold, including, by the one or more processors, the first food item in the ordered list of food items arranged by the final score.

6. The computer-implemented method of claim 1, wherein the ordered list of food items from the aggregate data arranged by the respective scores of the food items includes optionally adding macronutrients and calorie information associated with the food items, respectively, as an output preparation of the ordered list of food items.

7. The method of claim 1, wherein triggering of the food detection event includes identifying the food items or a food establishment location from the input data received from the sources of input data that include camera devices and physical, audio, and GPS sensors.

8. A computer program product for detecting a food item consumed by a user, the computer program product comprising:
one or more computer-readable storage media, and program instructions stored on the one or more computer-readable storage media, the program instructions comprising:
program instructions to receive input data associated with possible food items for consumption by a user from at least one input source, wherein, the at least one input source includes a sensor communicatively connected to the one or more processors;
triggering, by the one or more processors, detection of a food detection event, based on the input data received from the sensors communicatively connected to the one or more processors;
in response to receiving metadata corresponding to the food detection events, program instructions to parse the input data of the food detection events using a predetermined first set of criteria, and parsing the metadata received using a predetermined second set of criteria, wherein the received metadata includes a time and a location of the food detection event associated with available shared data from parallel applications and application programming interfaces (APIs) communicatively connected to the one or more processors during the food detection event;
program instructions to create aggregate data for a first food item identified from a first food detection event by combining first input data of the first food item with the corresponding metadata of the first food detection event;
program instructions to calculate a first score associated with a probability the first food item of the first food detection event is consumed by the user, wherein calculation of the first score includes the input data received from the sensors and weighting factors determined from the metadata including the available shared data;
program instructions to generate an ordered list of the food items arranged by scores from the aggregate data of the food detection events, including the first food item from the first food detection event arranged by the first score; and
program instructions to format the ordered list of the food items consumed by the user into a predetermined form.

9. The computer program product of claim 8, wherein the predetermined first set of criteria includes a corpus of food terms and phrases that is accessed to identify food items by program instructions to compare the input data to the corpus of food terms and phrases, and the predetermined second set of criteria includes recorded time data corresponding to the food detection event, location and proximity at the time of the food detection event, and application input from parallel operating apps on a user's device.

10. The computer program product of claim 8, wherein the input data from at least one of the plurality of sources include the input data from a group consisting of audio input data, image input data, text input data, and physical sensor input data.

11. The computer program product of claim 8, wherein the first score associated with the probability the first food item is consumed by the user further comprises:
program instructions to determine a time score for a time element of the metadata based on a comparison of the time associated with the first food detection event and known times the user typically eats;
program instructions to determine a location score for a location element of the metadata based on a proximity of the location of the first food detection event to a location of known food establishments;
program instructions to determine an app score for other applications of the metadata based on a type of the other applications; and
program instructions to determine a past data score for data of the confirmed prior food detection events, based on completion status and similarity of past event metadata compared to the metadata associated with the first food detection event.

12. The computer program product 8, further comprising:
program instructions to define a pre-determined threshold score associated with the probability that the user consumed the first food item;
program instructions to determine whether a final score associated with the first food item of the first food detection event exceeds the pre-determined threshold score associated with the probability that the user consumed the first food item; and
in response to determining the final score associated with the first food item of the first food detection event exceeds the pre-determined threshold, program instructions to include the first food item in the ordered list of food items arranged by the final score.

13. The computer program product of claim 8, wherein program instructions to arrange the ordered list of food items by the respective scores of the food items includes optionally adding macronutrients and calorie information associated with the food items, respectively, as an output preparation of the ordered list of food items.

14. The computer program product of claim 8, wherein triggering of the food detection event includes program instructions to identify the food items or a food establishment location from the input data received from the sources of input data that include camera devices and physical, audio, and GPS sensors.

15. A computer system for detecting a food item consumed by a user, the computer system comprising:
one or more processors;
one or more computer-readable storage media, and program instructions stored on the one or more computer-readable storage media, the program instructions comprising:
program instructions to receive input data associated with possible food items for consumption by a user from at least one input source, wherein, the at least one input source includes a sensor communicatively connected to the one or more processors;
triggering, by the one or more processors, a food detection event, based on the input data received from the sensor communicatively connected to the one or more processors;
triggering, by the one or more processors, detection of a food detection event, based on the input data received from the sensors communicatively connected to the one or more processors;

in response to receiving metadata corresponding to the food detection event, program instructions to parse the input data of the food detection event using a predetermined first set of criteria, and parsing the metadata received using a predetermined second set of criteria, wherein the received metadata includes a time and a location of the food detection event and metadata associated with available shared data from parallel applications and application programming interfaces (APIs) communicatively connected to the one or more processors during the food detection event;

program instructions to create aggregate data for a first food item identified from a first food detection event by combining first input data of the first food item with the corresponding metadata of the first food detection event;

program instructions to calculate a first score associated with a probability the first food item of the first food detection event is consumed by the user, wherein calculation of the first score includes the input data received from the sensors and weighting factors determined from the metadata including the available shared data;

program instructions to generate an ordered list of the food items arranged by scores from the aggregate data of the food detection events, including the first food item from the first food detection event arranged by the first score; and program instructions to format the ordered list of the food items consumed by the user into a predetermined form.

16. The computer system of claim 15, wherein the predetermined first set of criteria includes a corpus of food terms and phrases that is accessed to identify food items by program instructions to compare the input data to the corpus of food terms and phrases, and the predetermined second set of criteria includes recorded time data corresponding to the food detection event, location and proximity at the time of the food detection event, and application input from parallel operating apps on a user's device.

17. The computer system of claim 15, wherein the input data from at least one of the plurality of sources include the input data from a group of input data sources consisting of audio input data, image input data, text input data, and physical sensor input data.

18. The computer system of claim 15, wherein the first score associated with the probability the first food item is consumed by the user further comprises:

program instructions to determine a time score for a time element of the metadata based on a comparison of the time associated with the first food detection event and known times the user typically eats;

program instructions to determine a location score for a location element of the metadata based on a proximity of the location of the first food detection event to a location of known food establishments;

program instructions to determine an app score for other applications of the metadata based on a type of the other applications; and program instructions to determine a past data score for data of the confirmed prior food detection events, based on completion status and similarity of past event metadata compared to the metadata associated with the first food detection event.

19. The computer system of claim 15, further comprising:

program instructions to define a pre-determined threshold score associated with the probability that the user consumed the first food item;

program instructions to determine whether a final score associated with the first food item of the first food detection event exceeds the pre-determined threshold score associated with the probability that the user consumed the first food item; and in response to determining the final score associated with the first food item of the first food detection event exceeds the pre-determined threshold, program instructions to include the first food item in the ordered list of food items arranged by the final score.

20. The computer system of claim 15, wherein triggering of the food detection event includes program instructions to identify the food items or a food establishment location from the input data received from the sources of input data that include camera devices and physical, audio, and GPS sensors.

* * * * *